(12) United States Patent
Vervuert et al.

(10) Patent No.: US 6,342,526 B1
(45) Date of Patent: Jan. 29, 2002

(54) METHOD FOR ENHANCING OR ACHIEVING TRAINING-INDUCED BRADYCARDIA WITH CARNITINE

(75) Inventors: I. Vervuert, Hannover; Ulrike Wedemeyer, Celle; Hans-Peter Sparleder, Hannover; Cornelia Chrobok, Müleim/Ruhr; Manfred Coenen, Hannover; Johein Harmeyer, Wennigsen, all of (DE)

(73) Assignee: Lonza Ltd., Basel (CH)

( * ) Notice: Subject to any disclaimer, the term of this patent is extended or adjusted under 35 U.S.C. 154(b) by 0 days.

(21) Appl. No.: 09/760,390
(22) Filed: Jan. 12, 2001
(30) Foreign Application Priority Data Sep. 18, 2000 (EP) .............................................. 00120382

(51) Int. Cl.$^7$ ..................... A61K 31/225; A61K 31/205
(52) U.S. Cl. ....................................... 514/547; 514/556
(58) Field of Search .................................. 514/556, 547

(56) References Cited

U.S. PATENT DOCUMENTS

| | | | | |
|---|---|---|---|---|
| 5,576,348 A | * | 11/1996 | Kuratsune et al. | 514/547 |
| 5,973,004 A | * | 10/1999 | Howard | 514/561 |
| 6,232,346 B1 | * | 5/2001 | Sole et al. | 514/561 |

* cited by examiner

Primary Examiner—Raymond Henley, III
(74) Attorney, Agent, or Firm—Darby & Darby

(57) ABSTRACT

Use of Carnitine for achieving or enhancing training-induced bradycardia in a mammal, particularly in a horse, most preferably in a trotter horse.

13 Claims, 3 Drawing Sheets

METHOD FOR ENHANCING OR ACHIEVING TRAINING-INDUCED BRADYCARDIA WITH CARNITINE

BACKGROUND OF THE INVENTION

1. Field of the invention

The present invention relates to the use of Carnitine for enhancing or achieving training-induced bradycardia in a human or in a mammal, preferably in a horse. It further relates to the use of Carnitine for strenghtening the equine heart. Another object of the invention is the use of Carnitine for manufacturing a pharmaceutical or nutritional preparation destined to enhance training induced-bradycardia in a human upon physical training.

2. Description of Related Art

In a number of mammalian species, especially in man, physical exercise aiming at increasing physical fitness leads to improved cardiac performance. Prolonged exercise causes an increase in heart size and stroke volume. As a result of these adaptations, the trained and strengthened heart contracts less often at the same work load while expelling the same amount of oxygenated blood which is conveyed to the tissues as before the onset of training. The cardiac minute volume (MV) which is the product of stroke volume (SV) and pumping rate (heart rate, HR) is usually unchanged at the same level of physical exercise before and after a training period. At rest and in the absence of physical stress the HR is markedly decreased after a period of physical training while the SV is concomitantly increased, thus keeping the MV essentially the same: SV×HR=MV. The lowering of HR at rest and during exercise is called training-induced bradycardia. It is caused by an enlargement of the heart upon training, said enlargement being due to an increase in volume of individual heart muscle fibres. Concomitantly, the filling volume of the heart and the stroke volume are increased (Scheuer, J. et al., Cardiovascular adaptations to physical training. Ann. Rev. Physiol. 1977, 39: 221).

A training-induced bradycardia is accompanied by an enhanced resistance to fatigue and better performance of the heart under maximal physical strain as compared to the untrained heart. This phenomenon is known since the early nineteen thirties and has since been confirmed in numerous studies. Even under graded, moderate physical stress, the heart of trained individuals will beat slower than that of the untrained individual (Schaible, T. et al., Effects of physical training by running or swimming on ventricular performance of rat hearts. J. Appl. Physiol. 1979, 46:854; Pechar, G. et al., Specificity of cardiorespiratory adaptation to bicycle and treadmill training. J. appl. Physiol 1974, 36:753). The HR reducing effect has been demonstrated for man and animals, being most pronounced during the first two to three weeks of training. Only a moderate further reduction is achieved thereafter which will almost cease after three to four months of continuous training. At this time the training-induced bradycardia can be regarded as maximal (Tipton, C., Training an bradycardia in rats. Am. J. Physiol. 1965, 209:1089; Scheuer J. et al ., Cardiovascular adaptations to physical training. Ann. Rev. Physiol. 1977, 39:221).

Whilst being most pronounced in man, training-induced bradycardia is not unique to man. The phenomenon has repeatedly been described for dogs and rats (Wyatt, H. et al., Influences of physical training on the heart of dogs. Circ. Res. 1974, 35: 883; Tipton, C., Training and bradycardia in rats, Am. J. Physiol. 1965, 209:1089; Codini, M. et al., Cardiac responses to moderate training in rats, J. Appl. Physiol. 1977, 42:262).

Quite in contrast, up to now, training-induced bradycardia has been literally unknown in the case of horses. Though this would be a much desired effect for racing horses (trotters), it has been futilely sought in a number of research projects (Bayly, W. et al., Am. J. Vet.

Res. 1983, 44:544; Skarda, R. et al., Am. J. Vet. Res. 1976, 37:1485; Fregin, G. and Thomas D. P., in: Equine Exercise Physiology. Eds. Snow, D. H. et al., Burlington Press Ltd./Cambridge 1983, 76; Persson, S. G. B. et al., in: Equine Exercise Physiology. Eds. Snow, D. H. et al., Burlington Press Ltd./Cambridge 1983, 458; Rose, R. J. et al., 1983, Vet. Rec. 113:612; Miller, P. A: and Lawrence L. M., in: J., Equine Exercise Physiology II, Eds. Gillespie, J. R. and Robinson, N. E., ICEEP Publications, San Diego, 1987, 476). This is likely due to the fact that horses have been evolutionary optimized for physical performance and endurance exercise upon running. In comparison to other animal species, the parasympathetic input into the equine heart is likely to be higher. This higher autonomic nervous input appears partly be responsible for the relatively low heart rate of horses at rest and during moderate intensities of exercise. An increased parasympathetic control of the equine heart is probably due to genetic factors, programming the organ to a relatively high standard of physical performance.

BRIEF SUMMARY OF THE INVENTION

It is an object of the present invention to achieve or enhance a training-induced adaptation effect of the heart of a human or of a mammal, in particular of the equine heart, leading to increased endurance and improved performance. This object is achieved by administering carnitine to a human or to a mammal concomitantly to physical training.

BRIEF DESCRIPTION OF DRAWINGS

Below, preferred embodiments of the present invention are explained in more detail by aid of the enclosed drawings, wherein.

DETAILED DESCRIPTION OF THE INVENTION

Figure 1:
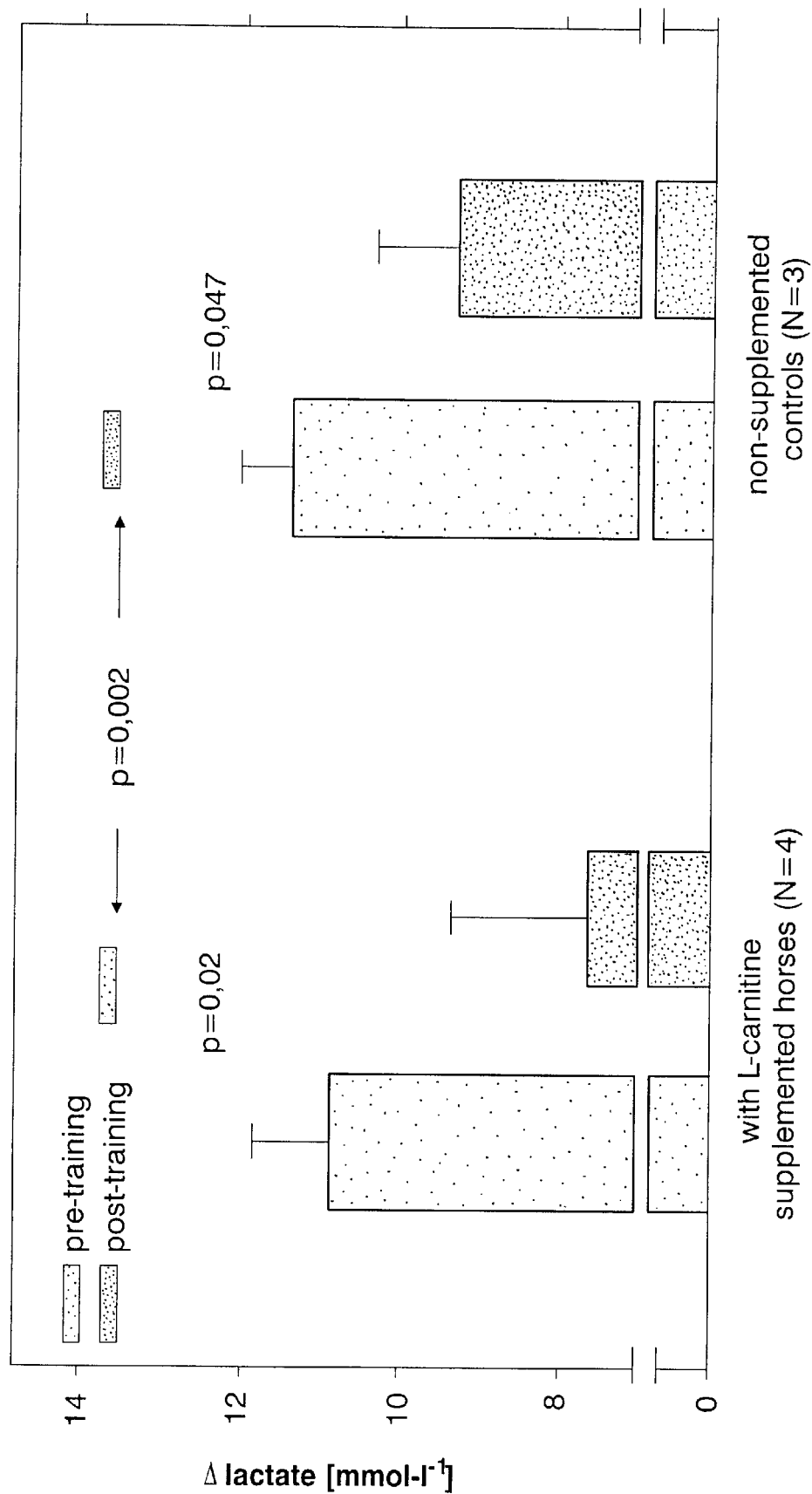
FIG. 1 shows the effect of physical exercise and carnitine supplementation on the training-induced increase in the concentration of lactate in blood of horses.

The use of carnitine enhances or achieves training-induced bradycardia in a human or mammalian individual. The mammal can be any mammalian animal such as e.g. horses, dogs, cats, rats, but does not comprise man. Preferably the mammal will be a horse, more preferably a trotter or racing horse. The carnitine may be racemic or, preferably, may be essentially pure L-carnitine (carnitine), or a corresponding alkanoyl-carnitine such as e.g. acetyl-carnitine or propionyl-carnitine, or a suitable, preferably non-hygroscopic, salt of such compounds such as e.g. L-carnitine tartrate, L-carnitine-magnesium-citrate, acetyl-L-carnitine tartrate, acetyl-L-carnitine-magnesium-citrate, or any mixture of the afore mentioned compounds. The bradycardia according to the present invention means any reduction of the frequency of heart beat, expressed as beats or pulses per minute, after a period of physical training as compared to the pulse rate of the untrained individual, before the onset of training. It refers to the resting pulse rate, i.e. the pulse rate of the individual at rest, in the absence of physical stress, but can also be observable by monitoring the heart rate at low and moderate levels of physical exercise. The training-induced bradycardia can be measured by coventional means for determining the heart rate (HR). A lowered pulse rate will lead to enhanced endurance and improved maximal performance upon graded physical work loads.

The term "training-induced" refers to a period of repeated physical exercises which the individual is subjected to, and which is accompanied by repeated administrations of carnitine to said individual during said period. Preferably, the training is an endurance training aimed at enhancing the physical fitness, such as any kind of running or racing over longer distances. It is well known that only during such exercises metabolism switches from initial glycolysis (achieved by breakdown of glykogen) to fatty acid oxidation. It is the latter process where carnitine exerts an important metabolic function, probably contributing to the changes in the structure and size of the heart that lead to bradycardia.

Further preferred is that the overall training period lasts at least one to two weeks, more preferably at least two weeks, meaning that physical exercise as e.g. endurance training is regularly or almost regulary performed, most preferably every one to two days during said period. In the case of horses, the quantitative extent of training-induced bradycardia as being achieved by carnitine administration will be lower than in other species, since training-induced bradycardia has been literally unknown in horses up to now. Therefore, the effect of carnitine is even more remarkable in horses, in that cardiac function of an animal that is genetically trimmed for maximum physical performance may surprisingly still further be enhanced by carnitine supplementation. In horses, the maximum cardiac effect will be observable after 4 weeks of training. Preferably, the horses according to the present invention are younger, untrained horses up to 3 years of age, more preferably of up to 2 years of age; the bradycardic effect according to the present invention is most pronounced in them. In horses, the enhanced physical performance resulting from the training-induced bradycardia may be observed as increase in the V200 value (Persson, S. G. B.. In: Equine Exercise Physiology, Eds. Snow, D. H. et al., Burlington Press Ltd./Cambridge 1983, 441), i.e. the running velocity of a horse at which its heart frequency rises to 200 beats per minute. Carnitine-evoked bradycardia will result in an increase of V200, meaning a higher racing speed (order of 600–730 metre/minute) as compared to a control group of horses not supplemented with carnitine.

Carnitine-supplementation according to the method of the present invention may be achieved by adding carnitine to commonly used feed mixtures, by adding carnitine to drinking water or by injecting or infusing pharmaceutically acceptable liquid preparations or solutions comprising carnitine, either intravenously or subcutaneously. Oral intake of carnitine, as a nutritonal supplement, is the preferred mode of working the present invention.

Preferred dosages required for achieving the training effect according to the present invention are in the range of 0.01 g to 30 g of carnitine per day for all species. However, particularly in the case of racing horses, dosages may amount up to 150 g carnitine per day or even more, without having toxic effects. Preferably, a daily dose of 0.001 to 0.2 g carnitine per kg body weight is taken up by the individual.

It is also possible, in other embodiments of the present invention, to further supplement the feed with other beneficial substances that have been reported to enhance cardiac function in conjunction with carnitine, e.g. Coenzyme Q or Coenzyme Q 10 in particular.

Training-induced bradycardia, more precisely, enhancement of training-induced bradycardia was equally achieved by carnitine administration upon experimentation with rats and swine. Since both animals are more similiar to man, carnitine-supplementation during periods of training will enhance or facilitate training-induced bradycardia in man, with the result of enhanced resistance to fatigue and improved performance under maximum levels of exercise.

It is a further object of the present invention to use carnitine for manufacturing a pharmaceutical or nutritional preparation destined to enhance training-induced bradycardia in a human upon physical training, concomittant with the consumption of said preparation. The preferred amount of carnitine for use in said preparation is in the range of 0.01 g to 8 g of carnitine, preferably in the range from 0.05 to 4 g of carnitine. The aspects of the invention described in the foregoing apply likewise.

Another object of the present invention is the use of carnitine for strenghtening the equine heart. In concert with the above said, training-induced bradycardia results in improved V200 performance and is achieved at the cellular level by growth of heart muscle fibers, thereby increasing the volume of said fibers (Scheuer, J. et al., ibd.; Ekblom, B. et al., Effect of training on circulatory response, J. Appl. Physiol. 1968, 24:518) and, in consequence, the ventricle volumes. The aspects of the invention described in the foregoing apply likewise.

EXAMPLE 1
Feed Preparation for Horses

An amount of 20 g of Carniking® is mixed with 1 to 5 kg of crushed oat containing concentrate ("Reformhafer®" Fa. Höveler. 40764 Langenfeld) and is offered to a horse in two or three portions per day for periods for 4 weeks. Carniking® contains 50 % of L-carnitine being absorbed to a silicate which serves as an inert support matrix. Depending on the size of the horse and upon its daily work loads the animal may receive 3 to 7 kg of good quality hay, 0,1 to 0.3 kg of a mineral mix which contains the essential macro minerals and micro nutrients including trace elements and vitamins. The animal may also be offered daily an amount of 0.1 to 0.3 kg of plant oil, preferably linseed oil and may have free access to salt lick. Water must be available at all times.

EXAMPLE 2
Nutritional Supplement for Human Consumption

A hard gelatine capsule is filled with approximately 500 mg of a fine-milled powder mixture. The powder mixture is prepared in a conventional knedding machine. The composition is made up of:

| | |
|---|---|
| L-Carnitine | 430 mg |
| Sodium stearate | 1.5 mg |
| microcrystalline cellulose | 20 mg |
| Polyvinylpyrrolidon | 20 mg |

Three capsules are ingested daily during a 2–3 weeks training period, said training consisting in a 10 km jogging exercise three times a week.

EXAMPLE 3
Evaluation of the Effect of Oral L-LC (LC) Supplementation during Exercise Training LC was obtained as commercially available free L-carnitine (Carniking® from Lonza Ltd.). After a first standardised exercise test (SET) during the whole experiment period (5 weeks training, 15 weeks detraining) a group of 4 Trotters received 10 g of LC/d offered with concentrate in two feed portions daily, as essentially described in example 1, while a group of 4 Trotters served as non-supplemented controls. All horses were two years old and were descendants from 1 stallion. The treadmill training program consisted of 8 aerobic, static exercise sessions (15 min warmup, 60 min exercise at an intensity level which maintained a blood lactate concentration of 2.0 mmol/l (VLA 2.0)) and 8 anaerobic exercise sessions (15 min, warm up, followed by 15 steps of graded exercise intensities of 1 min duration each, starting at VLA 4.0). During the dynamic exercises running speed was incremented every minute by 0.3 m/s and ranged from about of 5 m/s to 14 m/s. The horses performed the aerobic and anaerobic exercises in alternating sequence at two days intervals with one day rest between exercises. The SET was repeated (second test) at the end of the 5 weeks training period with seven horses FIG. 1 shows the effect of training and carnitine supplementation on the exercise-induced increase in the concentration of blood lactate.

Muscle biopsies from M. glutaeus med. and venous blood samples were collected at the beginning ($1^{st}$ SET) and the end of training ($2^{nd}$ SET) and at the beginning and the end of the $1^{st}$ (beginning of training) and $8^{th}$ (end of training) static and dynamic exercise and after 5 and 10 weeks of detraining. Venous blood samples were also collected during the two SETs at each graded speed increment. Heart rates were continuously monitored during exercises with a polar horse tester.

LC supplementation elevated LC concentration in M. glutaeus med. during five weeks of supplementation about 50% (from 3.2 to 4.6 mol/kg DM). LC concentration in the muscle remained at this high level during the whole detraining period. Among other effects, LC supplementation significantly influenced concentrations of glucose in plasma during the second SET, i.e. at the end of training (ANOVA, repeated measures). The horses supplemented with LC showed lower concentrations of glucose in plasma during exercise when compared with values from the first SET. No such changes were seen in the non-supplemented group of horses. The exercise-induced increase of blood lactate was also lower in the LC supplemented horses FIG. 1.

Figure 2:
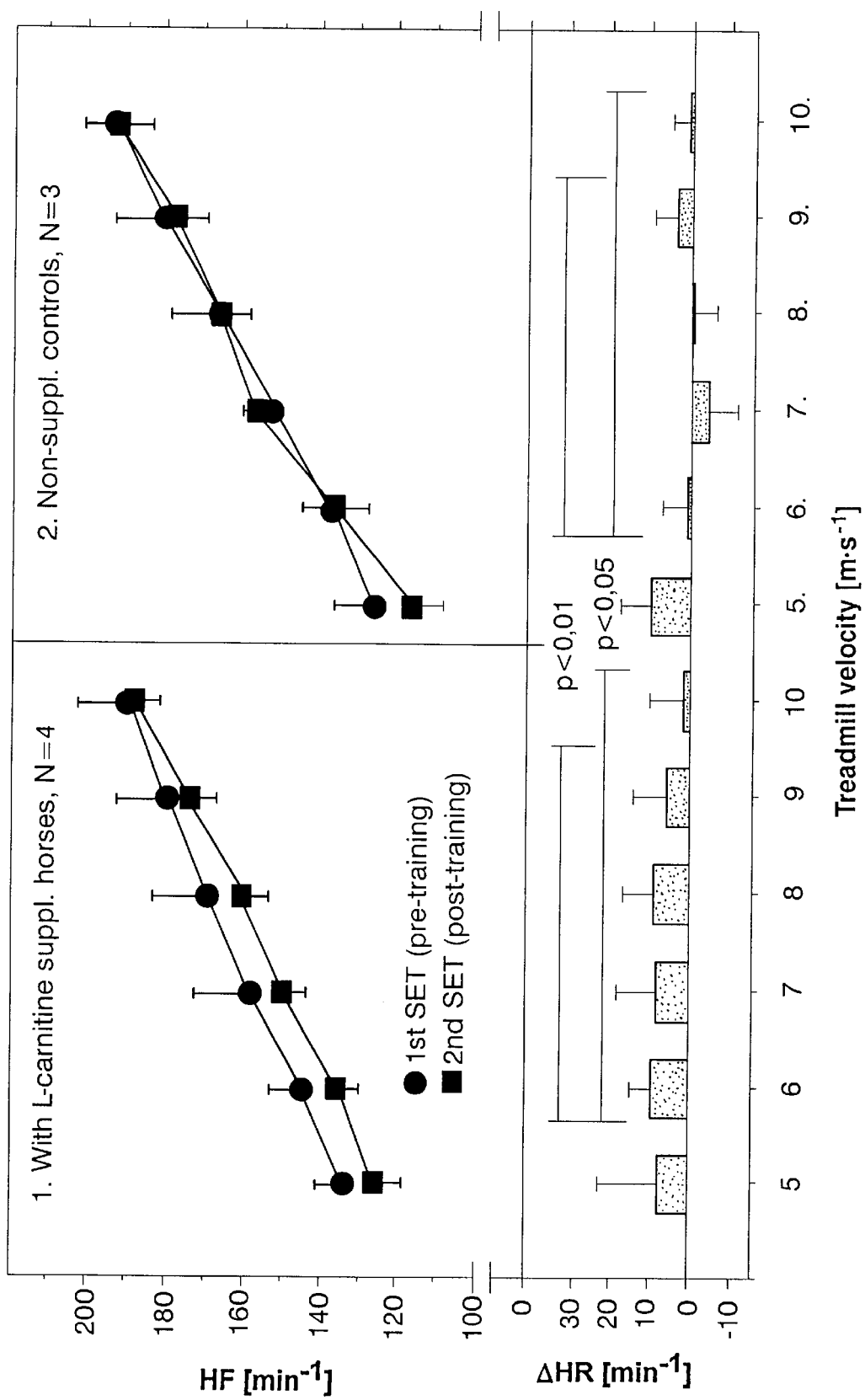
FIG. 2 shows the training-induced increase of heart rate (HR) of horses with and without carnitine supplementation during exercise test

Most importantly, at the end of exercise training period the group of horses supplemented with L-carnitine displayed a significant ($p<0.001$) reduction in heart rate at increasing levels of exercise work loads (treadmill speeds from 5 to 9 m/s) when compared with the start of training period (FIG. 2). No such reduction was observed in the control group of horses. In fact, post- training heart rate in the carnitine supplemented horses at equivalent work loads as at the start of training had declined by 7 beats/minute (FIG. 2). In the group of control horses the pre- and post-training exercise-related heart rates remained essentially unchanged. It should be noted from FIG. 2 that the lowering effect of heart rate was observable under a broad range of sub-maximal levels of dynamic exercises. The effect will be most useful for racing horses.

Figure 3:
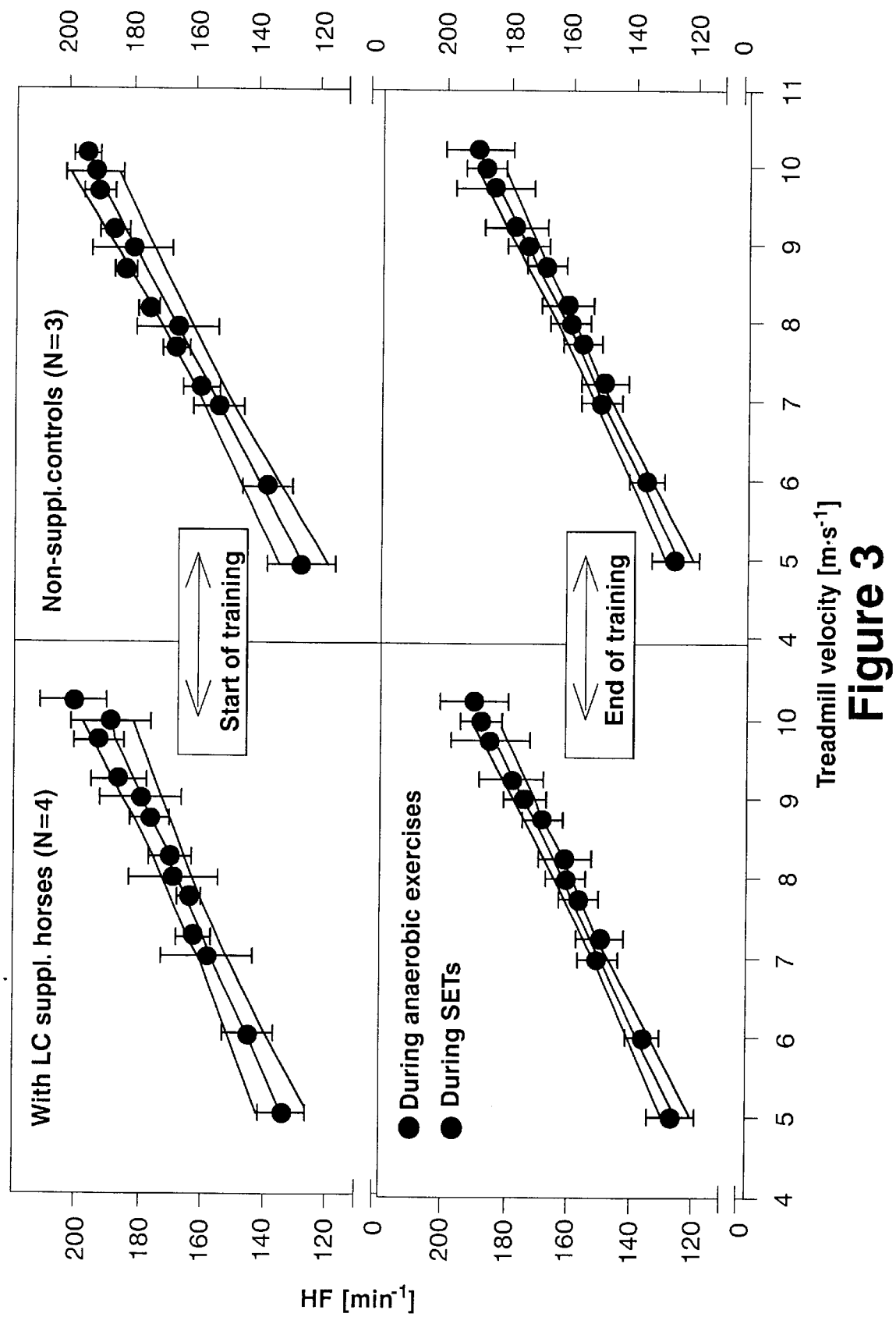
FIG. 3 shows the heart rate (HR) of horses during different types and different levels of physical exercise.

In horses the heart rate during a given level of exercise represents a useful indicator for evaluation of the degree of physical strain put upon the animal. This is shown in FIG. 3 The heart rates of horses from different types of exercise (SET or anaerobic training) at a given level of intensity are all located within the same range.

FIG. 1 shows the effect of training and carnitine supplementation on the exercise-induced increase in the concentration of lactate in blood of horses. Blood samples from the start of training (green) blood samples from the end of training (red). Four horses were supplemented with 10 g L-carnitine over a period of 5 weeks (left). Three control horses received no L-carnitine (right).

FIG. 2 shows the exercise-induced increase of HR during the first and second SET from 4 horses supplemented with L-carnitine (left, 1) and from 3 control horses (right, 2), given as mean value±SD. Hatched bars: post-training. Non-hatched bars: pre-training. Means of heart rates were calculated from 12 single measurements for each level of treadmill velocity. Y-axis: (top) HR ($min^{-1}$) and (bottom) ΔHR ($min^{-1}$), x-axis: treadmill speed (m/s).

In the lower half of the diagram the difference in HR (ΔHR-mean±SD) between the first and the second SET is shown as bars. Significant differences (p-values) of equivalent work loads between the supplemented and the control group are shown in the bottom section of the diagram.

FIG. 3 shows the HR of horses during different types (SET or anaerobic training) and different levels (treadmill velocity) of physical exercise. Four animals (left) were supplemented for five weeks with 10 g of L-carnitine/d, three control horses (right) received no L-carnitine. The heart rates are plotted versus the level of exercise intensity (treadmill speed) at the start of the training period (upper half) and at the end of the training period (lower half). Arithmetic means with standard deviations (SD) and the 95 % confidence limit of the mean are given. The heart rates which the horses assume at a given level of exercise intensity is a reproducible indicator of the physical strain put upon the animal.

Table 1 shows pre- and post-training heart rates (HR beats/min) - top: during a moderate level of aerobic exercise and - bottom: at the start and the end of incremented anaerobic exercises in horses supplemented with L-carnitine (N=4) and in control animals (N=3). The aerobic intensity exercise involved a warm up period of 15 min followed by 60 min trotting on a treadmill at constant blood lactate concentration of 2.0 mmol/l (VLA 2.0). The anaerobic high intensity exercise involved a warm up period of 15 min followed by 15 min of graded levels of exercise (incremented 15 steps TROTT or gallop of 1 min duration each). This period started with an exercise intensity corresponding to 4.0 mmol/l of blood lactate (VLA 4.0). The treadmill speed was incremented every minute (15 times) by 0.3 m/s.

The training period was five weeks of duration. Values are given as means with standard deviation, calculated from 12 consecutive HR measurements. VLA 2.0 and VLA 4.0 are individual measurements.

TABLE 1

| Time of measurement during moderate intensity intensity (aerobic) exercise | No. of horses | | Heart rate (beats/min) | |
|---|---|---|---|---|
| | L-C suppl. | control group | L-carnitine suppl. group | control group |
| pre-training | 4 | 3 | 130 ± 7 | 128 ± 10 |
| post-training | 4 | 3 | 122 ± 6 | 124 ± 8 |
| during incre- | | | start      end | start      end |

TABLE 1-continued

| Time of measurement during moderate intensity (aerobic) exercise | No. of horses | | Heart rate (beats/min) | |
|---|---|---|---|---|
| | L-C suppl. | control group | L-carnitine suppl. group | control group |
| mented, high intensity (anaerobic) exercise | | | | |
| pre-training | 4 | 3 | 150 ± 17 | 209 ± 13 | 150 ± 10 | 202 ± 6 |
| post-training | 4 | 3 | 143 ± 12 | 196 ± 11 | 145 ± 9 | 198 ± 8 |

What is claimed is:

1. A method of enhancing or achieving training-induced bradycardia in a mammal by administration of carnitine to said mammal.

2. The method of claim 1, herein the mammal is concomitantly engaged in a period of physical training.

3. The method of claim 1, wherein the carnitine is taken up orally.

4. The method of claim 1, wherein a daily dose of 0.001–0.2 g carnitine per kg body weight is taken up by the mammal.

5. The method of claim 1, wherein the carnitine is L-carnitine, an alkanoyl-L-carnitine or a salt thereof or any mixture of said compounds.

6. The method of claim 2, wherein the training is an endurance training.

7. The method of claim 6, wherein the period of training extends over at least two weeks, comprises physical exercise every one to two days and administration of a daily dose of carnitine during the entire period of training.

8. The method of claim 1, wherein the mammal is a horse or a trotter horse.

9. A method of strengthening the equine heart of a horse by administration of carnitine to said horse.

10. The method of claim 9, wherein the horse is concomitantly engaged in trotting or racing training.

11. A method of improving cardiac function of the heart of a horse by administration of carnitine to said horse.

12. The method of claim 1, wherein the mammal is a human.

13. The method of claim 6, wherein the endurance training is jogging or running training.

* * * * *